United States Patent [19]

Jeffcott et al.

[11] Patent Number: 4,976,267

[45] Date of Patent: Dec. 11, 1990

[54] METHOD AND APPARATUS FOR THE MEASUREMENT OF BONE QUALITY IN VIVO

[75] Inventors: Leo B. Jeffcott, Werribee; Ronald N. McCartney, Dural, both of Australia

[73] Assignee: The University of Melbourne, Parkville, Australia

[21] Appl. No.: 220,083

[22] Filed: Jul. 18, 1988

[30] Foreign Application Priority Data

Jul. 16, 1987 [AU] Australia ................ PI3216

[51] Int. Cl.$^5$ ............................................ A61B 10/00
[52] U.S. Cl. ........................ 128/660.01; 128/660.02; 128/774
[58] Field of Search .................... 128/774, 24 A, 128/661.02, 661.03, 660.02

[56] References Cited

U.S. PATENT DOCUMENTS

| | | | |
|---|---|---|---|
| 4,580,574 | 4/1986 | Gavish | 128/661.03 |
| 4,625,555 | 12/1986 | Fujii | 128/661.02 |
| 4,635,198 | 1/1987 | Hohlweck et al. | 128/660.02 |
| 4,655,228 | 4/1987 | Shimura et al. | 128/661.03 |

FOREIGN PATENT DOCUMENTS

| | | | |
|---|---|---|---|
| 8002796 | 12/1980 | PCT Int'l Appl. | 128/661.03 |
| 8707494 | 12/1987 | PCT Int'l Appl. | 128/661.03 |

OTHER PUBLICATIONS

Ruff & Hayes, "Bone-Mineral Content in the Lower Limb", Sep., 1984, The Journal of Bone and Joint Surgery, vol. 66-A, No. 7, pp. 1024-1031.

Schryver, Hintz & Lowe, "Calcium Metabolism, Body Composition, and Sweat Losses of Exercised Horses", Feb. 1978, Am J Vet Res, vol. 39, No. 2.

Greenfield et al., "Measurement of the Velocity of Ultrasound in Human Cortical Bone in Vivo", Mar. 1981, Radiology, vol. 138, No. 3, pp. 701-710.

Piotrowski, G., "Geometric Properties of Equine Metacarpi", Jun., 1981, J. Biochemics, vol. 16, No. 2, pp. 129-139.

Primary Examiner—Kyle L. Howell
Assistant Examiner—John D. Zele
Attorney, Agent, or Firm—Dennison, Meserole Pollack & Scheiner

[57] ABSTRACT

A method of determining in vivo an estimate of the modulus of elasticity of a bone. The method including the steps of applying an ultrasound beam to a limb from a transmitting transducer to a receiving transducer, and then measuring the flight times, $T_s$ for an ultrasound beam along a first path through the cortex of the bone, and $T_m$ along a second path through the cortex and medulla of said bone. After performing these steps, the method calculates the diameter X of the bone from the external diameter of the limb minus a predetermined constant allowing for skin and flesh, calculates the apparent velocity $C_a$ from X divided by $T_s$, calculates the mean velocity V from X divided by $T_m$, and calculates the cortical bone velocity $C_{bE}$ from a predetermined function f multiplied by $C_a$. Next, the method determines a ratio R for the diameter of the medulla to the diameter of the cortex and then estimates the cross-sectional area $CSA_E$ of the bone from the values of the diameter X, the ratio R and from predetermined constants. From these derivations, the bone mineral content, BMC, the estimated compact bone density, $CBD_E$, and an estimate of the modulus of elasticity from the product of $CBD_E$ and $C_{bE}$ are determined.

6 Claims, 5 Drawing Sheets

AREA FORMULAE:

Ellipse $= \frac{\pi}{4} \cdot A \cdot B$

Medulla $= \frac{\pi}{4} \cdot Y \cdot L.Y$ $= \frac{\pi}{4} \cdot L \cdot Y^2$ $= \frac{\pi}{4} \cdot X \cdot K.X.$   Area of medulla Cortex $= \frac{\pi}{4} (K.X^2 - L.Y^2)$ $= \frac{\pi}{4} \cdot X^2 (K - L.R^2)$

METHOD AND APPARATUS FOR THE MEASUREMENT OF BONE QUALITY IN VIVO

FIELD OF THE INVENTION

This invention relates to methods and apparatus for the measurement of bone quality, in vivo. While a preferred embodiment of the invention will be described as applied to the measurement of bone quality in horses, the invention is equally applicable to the performance of similar measurements in humans and other animals.

BACKGROUND OF THE INVENTION

Assessment of bone quality can be derived from measurements of bone mineral density (BMD kg m$^{-3}$), compact bone density (CBD kg m$^{-3}$) and a modulus of elasticity (J GN m$^{-2}$). BMD can be derived from the bone mineral content (BMC kg m$^{-1}$) if the cross sectional area is known. BMC can be determined using single photon absorptiometry with the ability to detect changes of less than 3%. Compact bone density (CBD kg m$^{-3}$) can be estimated using a bone model (Greenfield et al 1981) from BMC, cross sectional area (CSA m$^2$) and estimated constants of the microscopic bone mineral density ($\rho_m$ kg m$^{-3}$), and collagen density ($\rho_c$ kg m$^{-3}$) by the equation:

$$CBD = \rho_c + (1 - \rho_c/\rho_m)BMC/CSA \qquad (1)$$

The modulus of elasticity cannot be easily determined in vivo, however a method that has received some attention involves the transmission of ultrasound through bone because the velocity of sound (C m s$^{-1}$) through a material is related to a modulus of elasticity and CBD, provided dispersive and attenuating effects are ignored by assuming the use of the Helmholtz equation:

$$J = CBD \cdot C^2 \qquad (2)$$

In bone both the density and modulus change with alteration of mineral content. However, it would appear that the change in ultrasound velocity reflects the change in modulus of elasticity more than the change in density. There are reports of the anisotropic nature of bone which is illustrated by different velocities of ultrasound in the axial, radial and tangential directions by reporting ratios of approximately 1.2:1.08:1. In this specification it is assumed that the transverse velocity in a direction at a right angle to the long axis of the bone is predominantly being estimated. An ideal bone for the development of these measurement techniques and for subsequent clinical testing is the third metacarpal bone of the horse. It is a reasonably large bone, easily accessable, has minimal surrounding tissues, is subjected to considerable biomechanical strain and has had its geometric and biomechanical properties studied.

There are essentially two types of bone that can be measured (i.e. cortical and trabecular or cancellous). Cortical bone is dense and compact contributing mainly to the strength of long bones, whereas trabecular bone has a faster turnover and more rapidly reflects generalized changes in the skeletal system (e.g. in osteoporosis). In man it is measurement of trabecular bone that is considered more important for the early detection of metabolic bone changes, however accurate cortical bone measurements are not ruled out.

In the present specification "bone quality" includes bone mass or density, measured as its mineral content, and stiffness as estimated by the modulus of elasticity. Both these parameters have been shown to be related to bone strength. Noninvasive measurements of bone mineral content have been considered of diagnostic importance for over 50 years. The current trend is not to use plain radiography, but to develop more sophisticated methods. A variety of different techniques for bone mineral content have been successfully used to quantify aspects of bone both clinically (e.g. in age-related osteoporosis) and experimentally (e.g. by immobilization and spaceflight).

To date measurements of ultrasound velocity in bone have been mainly in cortical bone and such measurement have not been applied clinically except in horses. These early techniques, are not as sophisticated as the technique to be described in the present specification and have not been widely implemented. Our own investigations have led us to believe that further exploitation of ultrasound as a modality for assisting in bone quality assessment is warranted.

In human medicine the clinical applications for assessment of bone quality have been well reported, particularly in the evaluation of osteoporosis and metabolic bone disease. A recent review article on imaging and measurement methods for Diagnostic Imaging indicates that dual photo absorptiometry and quantitative CT are the only methods listed for bone quality measurements. Other emerging techniques, not reported in this article, include Positron Emission Tomography (PET), Single Photon Emission Computer Tomography (SPECT) and Magnetic Resonance Imaging (MRI). However, all of these modalities have high capital costs, are available only in large medical departments and result in a moderate to high fee for service.

The application of some of these techniques to the horse also has great potential, particularly for accurate assessment of skeletal maturity and to monitor the effects on bone of exercise and training methods. It has been clearly demonstrated that increased mechanical loading of the skeleton leads to increased bone mass and strength.

Ultrasound velocity of bone can be used to measure bone quality because it is directly related to its stiffness or elasticity and its density or specific gravity as described in equation 2.

The modulus of elasticity (J) is the property of a material which relates to its bending strength and stiffness and ultimately to its fracture threshold.

Preliminary studies using transverse ultrasound velocity through the metacarpal shaft of the horse, to give an indication of J, have been encouraging. The method involves passing a beam of ultrasound transversely from a transmitting to a receiving transducer. Two 2.25 MHz transducers, mounted on a digital caliper to give a readout of their distance apart, are placed on either side of the bone. After amplification of the signal by up to 90 decibels (dB), an electrical image of the ultrasound beam leaving one transducer and arriving at the other is recorded on an oscilloscope. The time of flight through the bone is then measured and, by knowing the distance between the transducers, the velocity of ultrasound (m s$^{-1}$) can be simply determined.

This value for ultrasound velocity is referred to as the "apparent transverse velocity" (Ca) because it assumes that the pathway of the ultrasound beam is directly between the two transducers. In fact, the fastest pathway of the ultrasound beam is confined to the cortex and passes around the medullary cavity. The ultrasound velocity through cortical bone (approx 3000 m s$^{-1}$) is double that through the medulla (approx 1500 m s$^{-1}$). Thus the actual distance travelled by the ultrasound beam is greater than the distance between the transducers. For this reason, an "apparent transverse velocity" measurement cannot be used to obtain a sufficiently accurate estimate of bone quality.

SUMMARY OF THE INVENTION AND OBJECTS

The object of this invention is to provide a practical and reproducible method for estimating the transverse cortical bone ultrasound velocity and the cross-sectional area which can then be used with absorptiometry measurements to make estimates of bone quality in vivo.

The invention therefore provides a method of determining in vivo an estimate of the modulus of elasticity of a bone, comprising the steps of passing a beam of ultrasound from a transmitting transducer through the bone to a receiving transducer, determining the distance between said transducers and correcting that distance to obtain a measure of the diameter of said bone, measuring the time of transmission of ultrasound beam along a first path through the cortex of said bone and along a second path through the cortex and medulla of said bone, calculating the velocity of said beam a long said first path and a long said second path and using said velocity values to calculate an estimate of the transverse cortical bone velocity and the ratio of the diameter of the medulla to the diameter of the cortex, calculating an estimate of the cross-sectional area of the cortex, measuring the bone mineral content of the bone and using said estimated cross-sectional area and said measured bone mineral content to calculate an estimate of the modulus of elasticity of the bone.

Experimental testing of the method defined above and described in greater detail below show that the estimated modulus of elasticity obtained by the method of the invention compares favorably with measured values for the same bone. Thus, by allowing for the fact that the ultrasound beam is transmitted a long two separate and distinct paths through the bone, a more accurate estimate of the modulus of elasticity of the bone may be obtained in vivo whereby the quality of the bone may be more accurately measured.

In performing the method according to the invention, a number of mathematical functions and constants must first be determined for the particular bone under investigation by experimental and mathematical means. For example, the mathematical relationship of the first path through the cortex of the bone may be specified as a factor (f) times the total diameter (X) of the bone, and the best empirical value for this factor so far determined is given by equation 10 as defined hereinafter.

Similarly, the velocity of sound in the medulla has been experimentally determined to be about 1470 ms$^{-1}$ and this value is deemed to be constant in the referred to calculations. In addition, the ovality of the external cortical bone cross section and the medulla must be taken into account. In the case of the third metacarpal bone in horses, observation has shown that the bone is approximately elliptical and empirical values for constants which take the ovality of the sections of the bone into account have been experimentally determined. In the case of the horse, a further factor is introduced to take into account the splint bones (MC2 and MC4) in the calculation of the cross-sectional area of the bone.

The presently preferred method will be described in greater detail below.

In another aspect, the invention provides an apparatus for determining in vivo an estimate of the modulus of elasticity of a bone comprising a pair of transducers for transmitting an ultrasound beam through the bone a long a first path through the cortex of said bone and a long a second path through the cortex and medulla of said bone, means for determining the distance between said transducers and for correcting that distance to obtain a measure of the diameter of said bone, means for determining the time of transmission of said ultrasound beam a long said first and second paths, means for calculating the velocity of said beam along said first and second paths and for calculating an estimate of the transverse cortical bone velocity and the ratio of the diameter of the medulla to the diameter of the cortex, and means for calculating an estimate of the cross-sectional area of the cortex and for calculating from this information and from separately derived information an estimate of the modulus of elasticity of the bone.

BRIEF DESCRIPTION OF THE DRAWINGS

A presently preferred embodiment of the invention will now be described with reference to the accompanying drawings in which.

DESCRIPTION OF THE INVENTION

Figure 1:
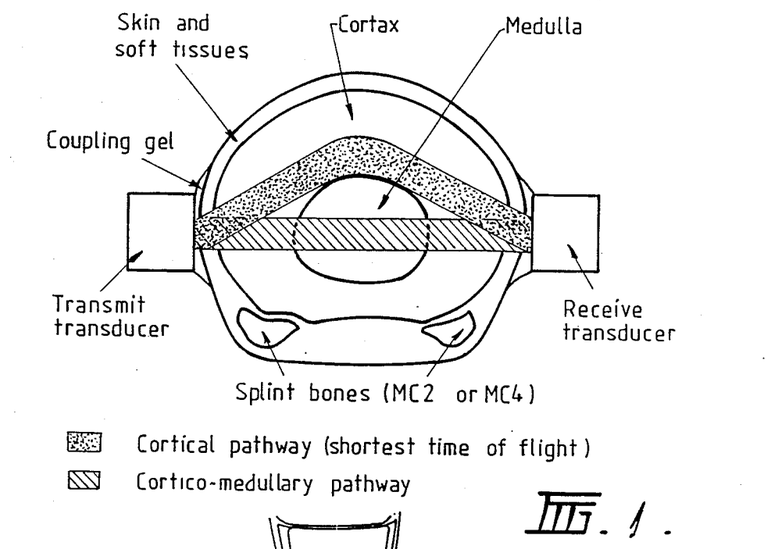
FIG. 1 is a diagrammatic representation of the ultrasound pathways through the cortex and through the cortex and medulla.

The estimate of ultrasound velocity is gained from knowing the distance between two transducers and measuring the time of flight of the transmitted beam. However, as the velocity of sound in the medulla is of the order 1500 ms$^{-1}$ and that in the cortical bone of the order of 3000 m s$^{-1}$ it is readily seen that the shortest time of flight must be for the sound to travel around the cortex (FIG. 1).

The mathematical relationship of this pathway should be able to be specified as a factor (f) times the total diameter (X) and also as a mathematical function of the ratio (R) of the diameter of the medulla (Y) to the diameter of the cortex (X):

$$\text{path length} = f.X = \text{function}(R) \quad (3)$$

Another pathway, the corticomedullary pathway, (FIG. 1) can be determined for the sound travelling through the cortical walls and the center of the medullas in a straight line. For this second pathway a mean velocity (V) can be determined from x/Tm (where Tm is the transmission time for the second pathway) and this is related to the bone velocity ($C_b$), the medullary velocity ($C_m$) and the ratio of medulla to cortex (R) by the formula:

$$R = Y/X = (C_b/V - 1)/(C_b/C_m - 1) \quad (4)$$

From the apparent velocity ($C_a$) which is the velocity determined from the shortest time of flight ($T_s$) and the corlical diameter (X), an estimate of the transverse cortical bone velocity ($C_{bE}$) can be made if the path length (f.X) is taken into account:

$$C_{bE} = f \cdot X/T_s = f \cdot C_a \quad (5)$$

Figure 2:
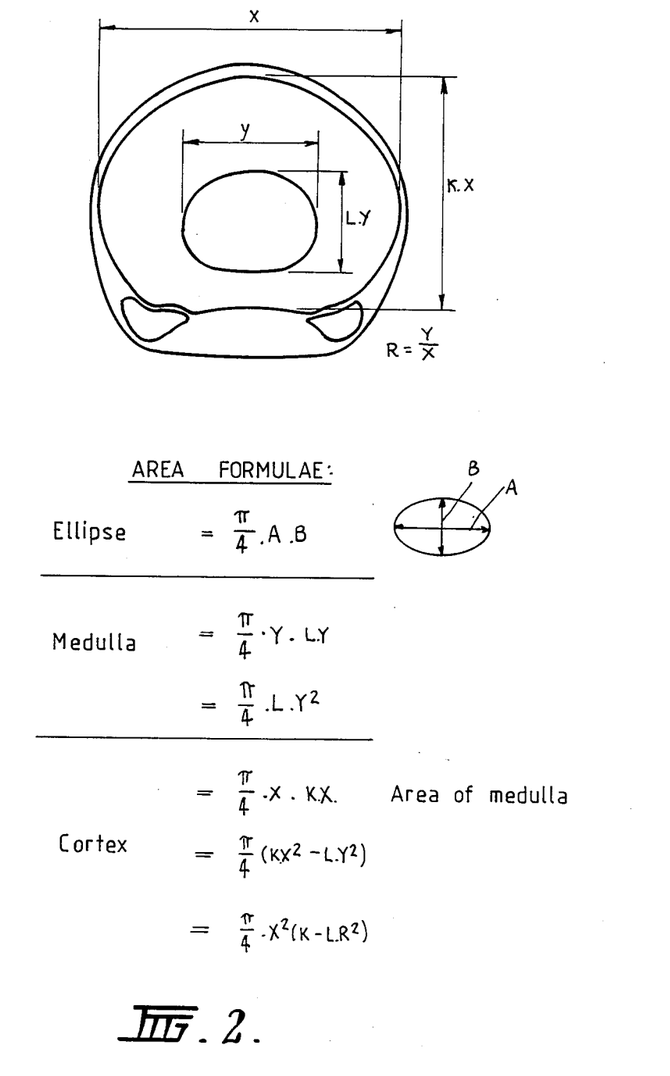
FIG. 2 is a diagrammatic representation of the assumption of ovality for the cortex and medulla.

$C_a$ is the first estimate of the transverse bone velocity and as the bone velocity must be greater than the apparent velocity, by iteration (appendix B), it is possible to calculate both $C_{bE}$ and R. An empirical formula by means of which f may be estimated will be found in equations (10) and (11). Seeing that the diameter of the bone X is known (transducer spacing minus the average skin and flesh thickness for the particular bone and position) and the ratio R estimated, the cross-sectional area of the cortex can also be estimated using the formula:

$$CSA_E = M \cdot \pi/4 \cdot X^2 (K - (L \cdot R^2)) \quad (6)$$

Where K is an ovality factor for the external cortical bone cross section and L is an ovality factor for the medulla. These ovality factors are derived from the bone cross sections on the assumption that the sections approximate ellipses as shown in FIG. 2. M is a factor to include the area of the splint bones (MC2 and MC4) as these bones were included in the determination of the BMC. Using this cross sectional area, BMC can be corrected to give an estimate of the bone mineral density ($BMD_E$) by:

$$BMD_E = BMC/CSA_E \quad (7)$$

Another estimate of the bone mineral density, $BMD_M$, can be determined from direct measurements by:

$$BMD_M = \text{ash weight/volume of wet bone} \quad (8)$$

The compact bone density, $CBD_E$, is estimated using equation (1). For this series the constant for $\rho_m$ was 3120 kg m$^{-3}$ and that for $\rho_c$ was 1310 kg m$^{-3}$ as published for bovine bone by Lees et al (1979). The $CBD_M$ can also be determined from direct measurement by:

$$CBD_M = \text{mass of wet bone/volume of wet bone} \quad (9)$$

The modulus of elasticity, $J_M$, is determined using equation (2), $CBD_M$ and $C_{bM}$. The modulus of elasticity, $J_E$, is determined with the same equation but using $CBD_E$ and $C_{bE}$.

Figure 1A:
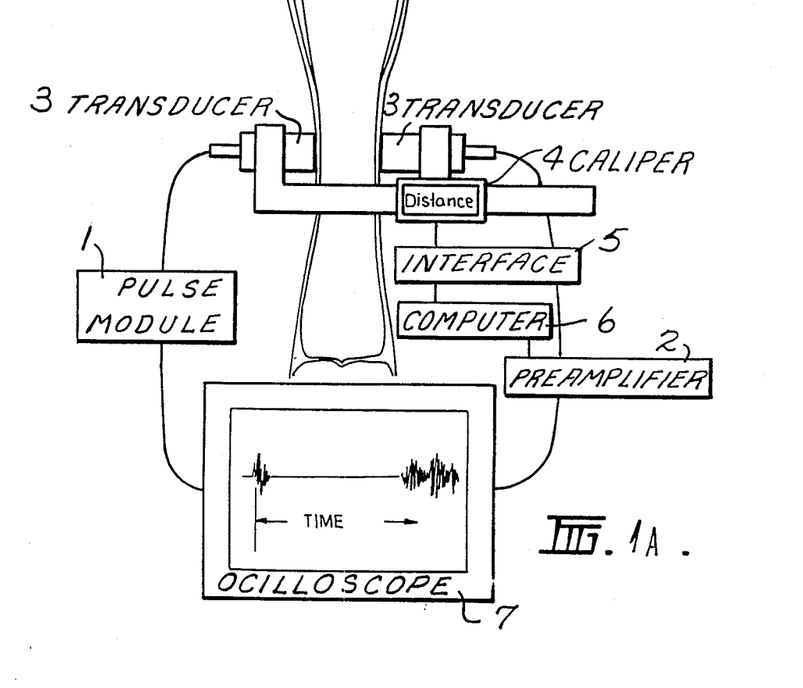
FIG. 1A is a schematic diagram showing the ultrasound and measuring apparatus.

Referring to FIG. 1A, the ultrasound time of flight measurements were obtained using a pulse module 1 (Panametrics Model 5055), a preamplifier 2 (Panametrics Model 5660B), connected to two 2.25 MHz, 13 mm diameter ultrasound transducers 3 (FIG. 1A) mounted on an electronic digital caliper 4 (Max-cal Model 950-101) connected to a computer (6) via an interface 5 (Mac-cal Model 960-101). A digital storage oscilloscope with signal averaging capacity 7 (Tektronix Model 468) is connected between the pulse module 1 and the preamplifier 2 to store and average the time of flight measurements. An Apple II Plus microcomputer was used to apply the various iterative and calculative algorithms described herein.

The BMC values were determined using a Norland Digital Bone Densitometer (Prototype Model 2781, Large Animal Scanning System, LASS) with an amercuim source ($^{241}$Am).

In summary, the method embodying the invention comprises the steps of (a) measuring the flight times for the ultrasound beam a long the two paths shown in FIG. 1, $T_s$, the flight time a long the cortical pathway using the oscilloscope 7 and Tm, the flight time a long the cortico-medullary pathway;

(b) calculating the diameter of the bone X from the distance between the transducers less a constant determined experimentally to allow for skin and flesh (in the case of the third metacarpal bone of a horse, 3 mm);

(c) calculating by means of the computer 6 the apparent velocity Ca from x/Ts (d) calculating by means the computer 6 the "mean" velocity V from x/Tm (e) calculating by means the computer 6 preferably by iteration, the values of $C_{bE}$ and R from equations (5), (10) and (4) respectively, Cm being treated as a constant determined experimentally to be approximately 1470 m s$^{-1}$;

(f) determining the cross-sectional area of the bone using formula (6) M, K and L being experimentally predetermined constants as described above;

(g) determining the bone mineral content BMC using a bone densitometer or by any other suitable method;

(h) determining the estimated compact bone density $CBD_E$ using equation (1);

(i) determining the modulus of elasticity using equation (2), $CBD_E$ and $C_{bE}$.

To test the theory outlined above, a series of 15 regular polymethyl methacrylate cylinders of diameter 50 mm and with central holes ranging from 15 to 35 mm in 2 mm steps were machined to simulate bone cross sections. Polymethyl methacrylate was chosen as its ultrasound velocity of about 2800 m s$^{-1}$ is close to that of bone at about 3000 m s$^{-1}$. The circular central hole was initially left empty to ensure only transmission through the polymethyl methacrylate and later filled with water which with a velocity of about 1500 m s$^{-1}$ closely approximated medullary tissue. Time of flight measurements were made on this group of cylinders to establish the best empirical relationship between pathway and ratio of medulla to cortex. Measurements taken with air in the central cavity confirmed that the pathway for the minimum time of flight is through the polymethyl methacrylate, whereas when filled with water both pathways were verified.

Figure 3:
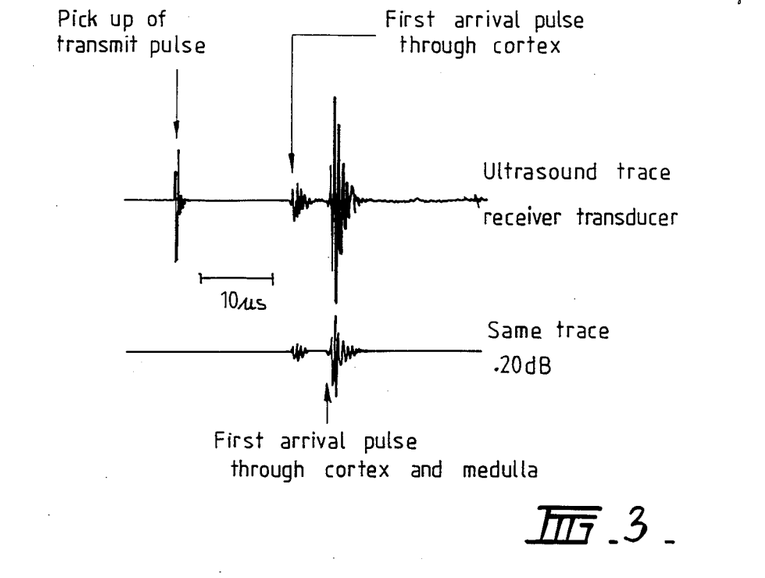
FIG. 3 is a diagrammatic representation of typical ultrasound traces used to determine the time measurements.
Figure 4:
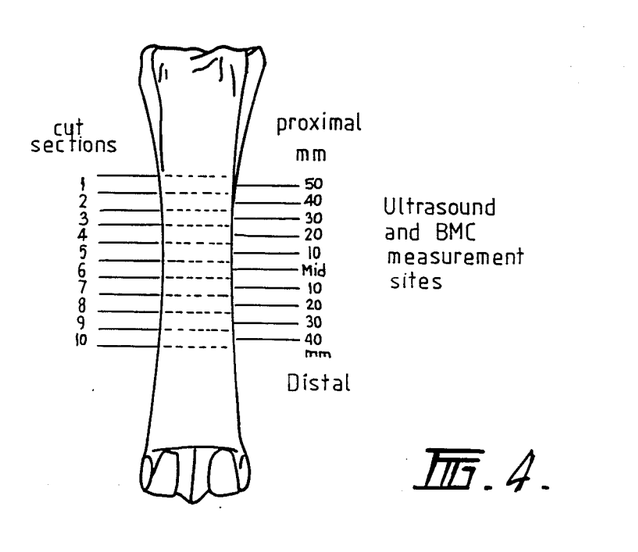
FIG. 4 is a diagrammatic representation of the ten measurement sites and sections for the ten selected left metacarpal bones.

Ten metacarpal bones of approximately the same size were selected from the left forelimbs of thoroughbred horses aged from 2 to 5 years. After removal of all soft tissues, the bones were stored at $-15°$ C. until examined. The lateral bone diameter, the times of flight through both the cortex a lone and the contico-medullary pathways (FIG. 3) and the BMC were determined at 10 sites a long the shaft of the bone as shown in FIG. 4. From these measurements $C_a$, R, $C_{bE}$ and $CSA_E$ (using factors determined later) were estimated. The bones were then cut to provide 10 transverse cross sections (FIG. 4). The transverse sections 1, 3, 5, 7 and 9 were cut using a band saw to provide approximately 1 cm thick sections and radiographed to record the cross-sectional profile. From these radiographic cross-sectional profiles an estimate of the ovality ratio of the cortical exterior (K) and the ovality ratio of the medulla (L) was determined to allow corrections to be made to estimate the cross-sectional area from the ultrasound measurements. The area of the splint bones (MC2 and MC4) relative to the area of the main shaft (MC3) was also estimated from the radiographs. For these sections the thickness (longitudinal length) was measured by digital calipers, the volume measured by a water displacement method and the cross section area ($CSA_M$) calculated. On the same sections $CBD_M$ (kg m$^{-3}$), ash mass (kg) and ash weight (kg/100 kg dry defatted bone) were measured. Out of the sections 2, 4, 6, 8 and 10, dorsal segments, of as large a size as practical, were cut to allow direct transverse cortical bone velocity measurements ($C_{bM}$) to be made. The bone marrow was removed as a plug from all bone sections and the ultrasound velocity of the bone marrow was determined in the dorsopalmar, lateral and longitudinal directions using the same ultrasound equipment.

The modulus of elasticity, J, was determined using equation (2) from two sets of measurements. The first estimate, $J_M$, is from the directly measured $C_{bM}$ and the directly measured $CBD_M$. The other estimate, $J_E$ was made from $C_{bE}$ and the $CBD_E$ from equation (1). Both determinations are made.

Figure 5:
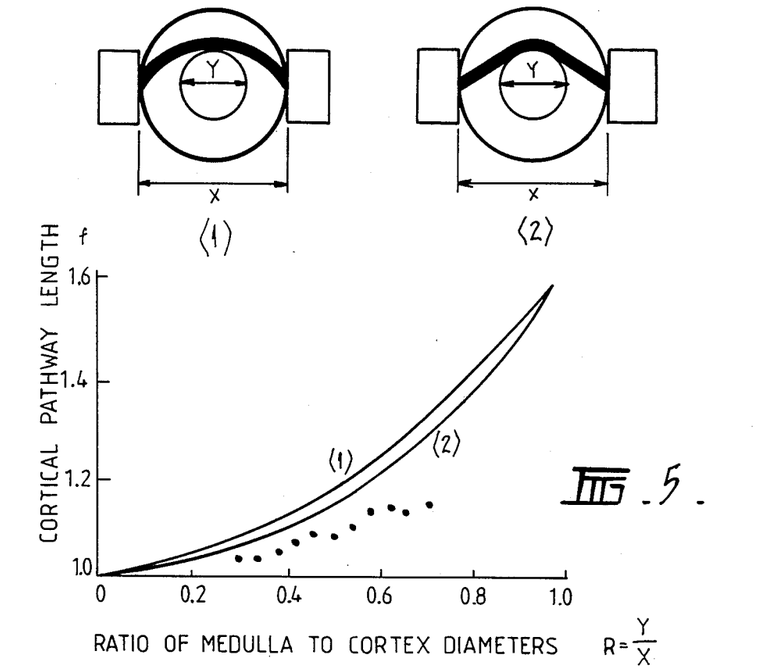
FIG. 5 is a graphical comparison of preliminary empirical pathways and experimental values for development of pathway lengths.

The pathway length determined on the polymethyl methacrylate blocks was compared with several mathematically derived theoretical pathways two of which are shown in FIG. 5. A suitable theoretical pathway based on physical principles has not yet been achieved. Various mathematical correction factors were then tested to find an empirical formula to allow estimation of the path length.

The best empirical formula so far determined is:

$$f = \sqrt{1 - R_c^2} + R_c \cdot \arcsin R_c \qquad (10)$$

where:

$$R_c = 0.78R \qquad (11)$$

Figure 6:
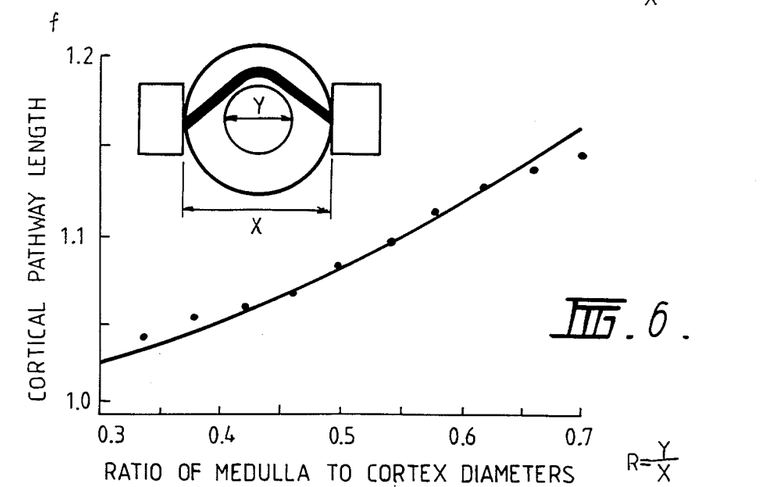
FIG. 6 is a graphical comparison of the best empirical formula for the ultrasound pathway length and experimental values.

This formula was used for all calculations on the selected bones. Equation (10) is shown with the experimental values in FIG. 6. A more accurate value for Rc determined by further experiments may be: Rc=0.79R (0.6+0.15R).

The measurements from the 100 bone marrow samples to determine the average medullary velocity ($C_m$) are summarized in Table 1. The average value of 1444±14 m s$^{-1}$ was used form subsequent calculations.

Figure 7:
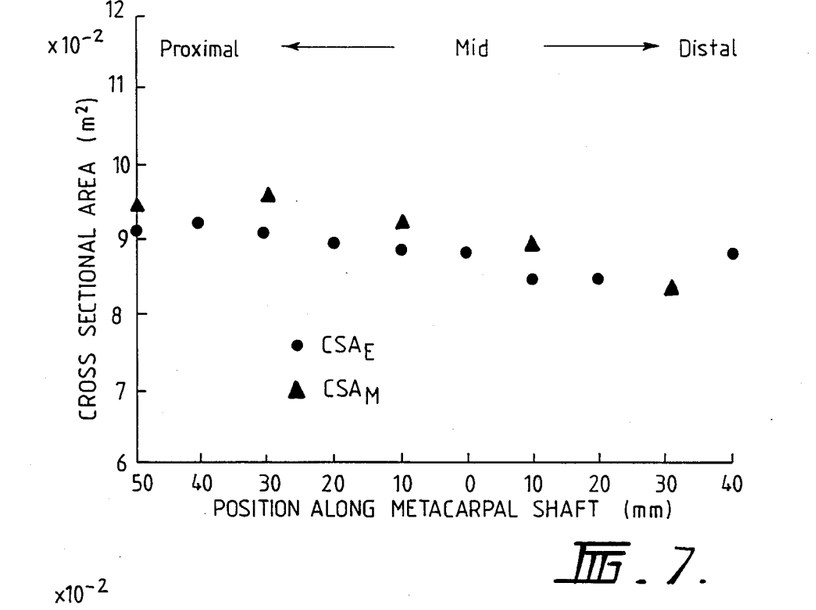
FIG. 7 is graphical comparison of experimental and measured cross-sectional areas of the bone under consideration.
Figure 8:
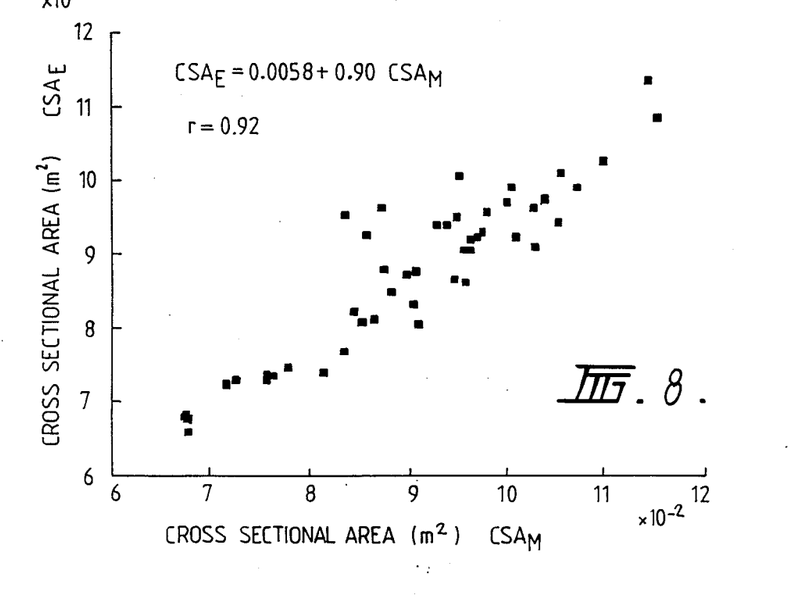
FIG. 8 is a graphical comparison of the experimental and measured cross-sectional areas for the experimental bone sections.

A comparison of $C_{bM}$ and $C_{bE}$ is summarised in Table 2. From the radiographs of the individual bone segments an estimate of ovality of the medulla and the ovality of the external cortical boundary was made. The average ovality factor for the medulla (L) of each bone (n=10) ranged over the 10 bones from 0.65 to 0.90 with a mean of 0.76. The average ovality factor for the cortex (K) ranged from 0.75 to 0.90 with a mean of 0.81. From the same radiographs the areas of the MC2, 3 and 4 were estimated by counting squares and average correction factors were determined for the sections a long the bones. Using these correction factors the cross-sectional areas were estimated from the ultrasound measurements and FIG. 7 shows $CSA_E$ versus $CSA_M$ for positions a long the shaft. FIG. 8 shows the result of a comparison for the 50 bone sites for sections 1, 3, 5, 7 and 9. For the same sections (n=5), Tables 3 and 4 summarize for each bone the average BMC (5 readings at each site), $BMC_M$, $BMD_E$, $CBD_M$, $CBD_E$, $J_M$ and $J_E$.

The above values for K, L and M are most valid for the middle region of the bone. The following table A lists corrections factors for K and L and new values for M according to the position of the testing site (the numbers correspond to the numbers in FIG. 4).

TABLE A

| BONE CUT SECTIONS | CORTEX K | MEDULLA L | SPLINT AREA M |
|---|---|---|---|
| 1 | 0.91 | 0.84 | 1.125 |
| 2 | 0.95 | 0.85 | 1.105 |
| 3 | 0.98 | 0.87 | 1.09 |
| 4 | 0.99 | 0.93 | 1.075 |
| 5 | 1 | 0.98 | 1.06 |
| 6 | 1 | 1 | 1.045 |
| 7 | 1 | 1 | 1.03 |
| 8 | 1 | 1.01 | 1.02 |
| 9 | 0.99 | 1.01 | 1.01 |
| 10 | 0.99 | 1.10 | 1 |

Estimates of the precision were obtained for $C_a$, $C_{bE}$, $CSA_E$ and BMC from multiple independent measurements taken at the same site of a bone. Using equations 1, 2, 7, 8 and 9 and estimates of the precision of the measurement of mass and length, further estimates using the method of propagation of errors were made for $CSA_M$, $BMD_E$, $BMD_M$ $CBD_E$, $J_E$ and $J_M$. These estimates are shown in Table 5.

The accuracy and precision of the methods used here for determining both transverse cortical bone velocity and bone mineral content are encouraging and correlate well with those of Greenfield et al (1981). Greenfield et al utilized the human radius and employed the same single beam photon absorptiometry, but used a pulse echo technique for cortical velocity measurement instead of the transmission method. Both of these ultrasound methods give similar results for cortical bone velocity. In man the cortical velocity of the radius is 3335±300 m s$^{-1}$ whereas for the equine metacarpus the velocity was measured at 3109±56 m s$^{-1}$. The advantage of the transmission method is that a lateral radiograph to measure cortical thickness is not required and an estimate of the cross-sectional area is obtained at the same time. Greenfield's estimate of uncertainty for cross-sectional area was 2-10% whereas by the transmission method the uncertainty for the equine metacarpus is about 5%. The variation of cross-sectional area with site and area of splint bones correlated well with the results published by Piotrowski et al (1983).

The estimation of cross-sectional area by the ultrasound method was considered good (correlation coefficient r=0.92) and proved to be better than just using an estimate of cross-sectional area based on diameter squared (r=0.82).

The values for bone mineral content in the horse differed from those in man because of the size of the bone being measured. An $^{241}$Am source was used instead of $^{125}$I. However, when the readings for bone mineral density (1060±20 kg m$^{-3}$) were compared with Greenfield et al (1120±150 kg m$^{-3}$) they were similar. The measurement of bone mineral density to this precision helps to overcome the volumetric problems identified by Ruff and Hayes (1984) found in using just bone mineral content.

The calculated estimates for transverse cortical bone velocity, bone mineral density, compact bone density and modulus of elasticity compared favorably with the measured values for the same parameters. Schryver (1978) measured the bending properties of the metacarpals of ponies and found the elastic modulus to be 18.4±0.14 GN m$^{-2}$ for the cranial cortex of the midshaft. He obtained values of 16.2 to 20.2 GN M$^{-2}$ for different parts of the cortex of the radius and femur and was able to show that diet, exercise and sex of the pony affected the elastic modulus, ultimate strength and energy absorption of the bone.

In this study the transverse cortical bone ultrasound velocity has been determined rather than the apparent transverse ultrasound velocity because it is more uniform along the shaft, is less subject to geometrical effects, allow an estimation of a modulus of elasticity and should provide better correlation between individuals.

These methods, having been developed on post mortem specimens, are now being applied to live animals. Ultrasound measurements (5 sites) take about 10 minutes per limb and absorptiometry (5 readings) takes about 20 minutes per limb. Using these combined techniques it will be possible to establish better parameters for skeletal maturity and to measure the effects of exercise on bone. Whilst these methods are being implemented in equine medicine there appears no reason why the same principles cannot be applied in humans. It will be appreciated that the use of the method to estimate the quality of various human bone would require the experimental determination of different constants (for example the ovality factors K and L would be replaced by different factors and the M factor would be omitted), but the method would otherwise be similarly applied.

APPENDIX A

Derivation of Formulae (a) Equation 4

$$T_m = \text{time through cortex} + \text{time through medulls} \quad (4)$$
$$X/V = (X - Y)/C_b + Y/C_m$$

dividing by $X$ and rearranging gives:

$$1/V = 1/C_b + R/C_m - R/C_b$$
$$R = (1/V - 1/C_b)/(1/C_m - 1/C_b)$$
$$= (C_b/V - 1)/(C_b/C_m - 1)$$

(b) Equation for curve (2) in FIG. 5 and leading to equation (10)

Assume geometrical symmetry, a straight line path across the cortex and an arc around the medulla.

Let $\theta$ equal angle between diameter (center to center of transducers) and straight pathway through cortex. $\theta$ is also half the angle of the arc.

Thus $\sin \theta = Y/X = R$ $$\text{Length of straight sections} = \sqrt{X^2 - Y^2}$$

-continued $$\text{Length of arc} = Y \cdot \theta \; (\theta \text{ in radian})$$
$$= Y \cdot \arcsin R$$

$$\text{Total length} f \cdot X = \sqrt{X^2 - Y^2} + Y \cdot \arcsin R$$

divided by $X$ gives $$f = \sqrt{1 - R^2} + R \cdot \arcsin R$$

(c) Equation for curve (1) in FIG. 5

Assume symmetry and that the sound path is along an arc of a circle which goes from center to center of the transducers and just touches the edge of the medulla as shown in the sketch. If S is the radius of curvature of the arc and 2 $\phi$ is the subtended angle of the arc then:

$$S - (X^2 + Y^2)/4Y = X \cdot (1 + R^2)/4R$$

and $$\sin \phi = X/2S = 2R/(1 + R^2)$$

the length of the arc $= 2 \cdot S \cdot \phi(\phi$ in radian$) = X \cdot ((1 + R^2) \cdot \arcsin(2R/(1+R^2)))/2R$ For this situation then $$f = ((1 + R^2) \cdot \arcsin(2R/(1+R^2)))/2R$$

APPENDIX B

The iterative procedure applied in a simple computer program involves equations (4), (5) and (10). $C_a$, V and $C_m$ are known leaving f, $C_b$ and R to be determined. The only restriction to the iterative process is imposed by equation (4) where:

$R = \infty$ when $C_b = C_m$
$R < 0$ when $V > C_b > C_m$
$R = 0$ when $C_b = V$
$R > 0$ when $C_b > V$ Provided the starting point of the iteration is with $C_b > V$ then the correct value is determined. $C_a$ is always greater than V and is used as the first estimate of $C_b$. The first estimate of R is then determined, equation (4), followed by the first estimate of f, equation (10). Equation (5) then gives a revised estimate of $C_b$. This process is continued until the change in $C_b$ per cycle is less than some chosen value e.g. 1 m s$^{-1}$. It takes only five cycles on average to achieve a suitable result.

APPENDIX C

Abbreviations f- factor to relate cortical pathway length to diameter of cortex.
f.X- path length of ultrasound beam through cortex of MC3.
K- ovality factor for external perimeter of cortex of MC3.
L- ovality factor for medulla of MC3.
M- factor to compensate for area of splint bones MC2 and MC4.
R- ratio of medulla to cortex of MC3=Y/X.
$R_c$- corrected ratio of medulla to cortex (R).
X- external diameter of cortex of MC3 (lateral).
Y- diameter of medulla of MC3 (lateral).
BMC- bone mineral content (kg m$^{-1}$).
$BMD_M$- measured bone mineral density (kg m$^{-3}$).

BMD$_E$- estimated bone mineral density (kg m$^{-3}$).
C- velocity of ultrasound (m s$^{-1}$).
C$_a$- apparent transverse cortical bone ultrasound velocity (m s$^{-1}$)—X/T$_s$.
C$_b$- transverse cortical bone ultrasound velocity (m s$^{-1}$).
C$_{bM}$- measured transverse cortical bone ultrasound velocity (m s$^{-1}$).
C$_{bE}$- estimated transverse cortical bone ultrasound velocity (m s$^{-1}$).
C$_m$- ultrasound velocity through medulla (m s$^{-1}$).
CBD$_M$- measured compact bone density or specific gravity (kg m$^{-3}$).
CBD$_E$- estimated compact bone density or specific gravity (kg m$^{-3}$).
CSA$_M$- measured cross-sectional area (m$^2$) (volumetric).
CSA$_E$- estimated cross-sectional area (m$^2$) (ultrasound).
J- modulus of elasticity.
J$_M$- estimated modulus of elasticity using CBD$_M$ and C$_{bM}$ (GN m$^{-2}$).
J$_E$- estimated modulus of elasticity using CBD$_E$ and C$_{bE}$ (GN m$^{-2}$).
p$_m$- microscopic bone mineral density (kg m$^{-3}$).
p$_c$- collagen density (kg m$^{-3}$).
MC 2, MC 3 and MC 4- second, third and fourth metacarpal bones of the horse.
T$_m$- time of flight for cortico-medullary path (s).
T$_s$- shortest time of flight of ultrasound transmission (s).
V- mean velocity of ultrasound through cortex and medulla (m s$^{-1}$). =X/T$_m$.

TABLE 1

Results of ultrasound velocity of the medulla (C$_m$ ± 1SD) measured in dorsopalmar, lateral and longitudinal directions of 10 metacarpal bones.

| Bone No. | C$_m$ - ULTRASOUND VELOCITY OF MEDULLA (m s$^{-1}$) | | | |
|---|---|---|---|---|
| | Dorsopalmar | Lateral | Longitudinal | Average |
| 1 | 1439 | 1451 | 1438 | 1443 |
| 2 | 1430 | 1441 | 1437 | 1436 |
| 3 | 1461 | 1469 | 1454 | 1459 |
| 4 | 1444 | 1453 | 1430 | 1439 |
| 5 | 1424 | 1432 | 1413 | 1423 |
| 6 | 1461 | 1461 | 1454 | 1459 |
| 7 | 1427 | 1437 | 1414 | 1423 |
| 8 | 1456 | 1464 | 1453 | 1458 |
| 9 | 1453 | 1465 | 1456 | 1458 |
| 10 | 1442 | 1460 | 1433 | 1445 |
| Average | 1444 ± 14 | 1453 ± 13 | 1438 ± 16 | 1444 ± 14 |

TABLE 2

Results obtained for directly measured (C$_{bM}$) and estimated (C$_{bE}$) transverse cortical bone velocity (±1SD) in 10 metacarpal bones.

| Bone No. | C$_b$ - CORTICAL ULTRASOUND VELOCITY (m s$^{-1}$) | | % difference between C$_{bM}$ and C$_{bE}$ |
|---|---|---|---|
| | C$_{bM}$ Directly Measured | C$_{bE}$ Estimated | |
| 1 | 3161 (±14) | 3155 (±35) | −0.19 |
| 2 | 3115 (±62) | 3164 (±51) | +1.57 |
| 3 | 3044 (±46) | 3150 (±29) | +3.48 |
| 4 | 3127 (±38) | 3104 (±43) | −0.74 |
| 5 | 3171 (±47) | 3196 (±45) | +0.79 |
| 6 | 3050 (±27) | 3060 (±30) | +0.33 |
| 7 | 3142 (±54) | 3247 (±37) | +3.34 |
| 8 | 3181 (±20) | 3115 (±37) | −2.07 |
| 9 | 3046 (±42) | 3082 (±29) | +1.18 |
| 10 | 3050 (±37) | 3061 (±20) | +0.36 |
| Average | 3109 (±56) | 3133 (±61) | +0.83 (±1.75) |

TABLE 3

Results (±1SD) of bone mineral content (BMC kg m$^{-1}$), measured and estimated bone mineral density (BMD$_M$ and BMD$_E$ kg m$^{-3}$), measured and estimated compact bone density (CBD$_M$ and CBD$_E$ kg m$^{-3}$) and ash weight (kg/100 kg dry defatted bone) in the metacarpal bones from 10 horses.

| Bone No. | BMC (kg m$^{-1}$) | BMD$_M$ (kg m$^{-3}$) | BMD$_E$ (kg m$^{-3}$) | CBD$_M$ (kg m$^{-3}$) | CBD$_E$ (kg m$^{-3}$) | Ash Weight (kg/100 kg dry bone) |
|---|---|---|---|---|---|---|
| 1 | 1.029 (±.045) | 1020 (±20) | 990 (±50) | 1890 (±10) | 1880 (±20) | 63.2 (±1.4) |
| 2 | 0.926 (±0.048) | 1100 (±40) | 1030 (±60) | 1920 (±30) | 1910 (±30) | 64.7 (±0.2) |
| 3 | 0.899 (±0.048) | 1050 (±10) | 1010 (±60) | 1880 (±30) | 1900 (±30) | 63.7 (±0.07) |
| 4 | 0.895 (±0.057) | 1050 (±130) | 1000 (±80) | 1890 (±10) | 1890 (±40) | 63.6 (±0.2) |
| 5 | 0.957 (±0.045) | 1080 (±20) | 1050 (±40) | 1910 (±20) | 1920 (±20) | 64.2 (±0.2) |
| 6 | 0.698 (±0.041) | 1050 (±10) | 990 (±20) | 1890 (±10) | 1880 (±10) | 63.1 (±0.1) |
| 7 | 1.018 (±0.042) | 1060 (±10) | 1080 (±30) | 1900 (±10) | 1940 (±10) | 62.3 (±0.05) |
| 8 | 1.004 (±0.029) | 1060 (±20) | 1060 (±40) | 1890 (±20) | 1920 (±20) | 63.4 (±0.02) |
| 9 | 0.851 (±0.030) | 1060 (±10) | 1080 (±30) | 1890 (±10) | 1940 (±10) | 62.8 (±0.02) |
| 10 | 0.715 (±0.045) | 1030 (±20) | 1000 (±30) | 1890 (±10) | 1890 (±10) | 61.7 (±0.6) |
| Average | 8.99 (±0.117) | 1060 (±20) | 1030 (±40) | 1890 (±10) | 1910 (±20) | 63.3 (±0.9) |

TABLE 4

Measured (J$_M$) and estimated (J$_E$) modulus of elasticity of the third metacarpal cortex from 10 horses.

| Bone No. | J$_M$ GN m$^{-2}$ | J$_E$ GN m$^{-2}$ | % diff. J$_M$ and J$_E$ |
|---|---|---|---|
| 1 | 18.8 (±0.2) | 18.7 (±0.6) | ±0.53 |
| 2 | 18.6 (±0.6) | 19.1 (±0.9) | 2.69 |
| 3 | 17.4 (±0.5) | 18.9 (±0.6) | 8.62 |
| 4 | 18.5 (±0.3) | 18.2 (±0.9) | −1.62 |
| 5 | 19.2 (±0.4) | 19.6 (±0.6) | 2.08 |
| 6 | 17.6 (±0.2) | 17.6 (±0.4) | 0 |
| 7 | 18.8 (±0.7) | 20.5 (±0.5) | 9.04 |
| 8 | 19.1 (±0.3) | 18.6 (±0.6) | −2.62 |
| 9 | 17.5 (±0.3) | 18.4 (±0.3) | 5.14 |
| 10 | 17.4 (±0.3) | 17.7 (±0.3) | 1.72 |
| Average | 18.3 (±0.7) | 18.7 (±0.9) | 2.45 (±4.04) |

TABLE 5

Estimates of ±1 SD for the precision of values determined in this investigation.

| DIRECTLY MEASURED VALUES | ESTIMATED VALUE |
|---|---|
| C$_a$ ± 0.32% (n = 41) | |
| BMC ± 1.15% (n = 20) | |
| C$_{bM}$ ± 1% | C$_{bE}$ ± 0.59% (n = 41) |
| CSA$_M$ ± 1.1% | CSA$_E$ ± 3.6% (n = 41) |
| CBD$_M$ ± 0.42% | CBD$_E$ ± 1.2% |
| BMD$_M$ ± 0.44% | BMD$_E$ ± 3.8% |
| J$_M$ ± 1.4% | J$_E$ ± 1.5% |

We claim:

1. A method of determining in vivo an estimate of the modulus of elasticity of a bone, comprising the steps of passing a beam of ultrasound from a transmitting transducer through the bone to a receiving transducer, determining the distance between said transducers and correcting that distance to obtain a measure of the diameter of said bone, measuring the time of transmission of the ultrasound beam along a first path through the cortex of said bone and along a second path through the cortex and medulla of said bone, calculating the velocity of said beam along said first path and along said second path and using said velocities to calculate an estimate of the transverse cortical bone velocity and the ratio of the diameter of the medulla to the diameter of the cortex, calculating an estimate of the cross-sectional area of the cortex, measuring the bone mineral content of the bone and using said estimated cross-sectional area and said measured bone mineral content to calculate an estimate of the modulus of elasticity of the bone.

2. A method of determining in vivo an estimate of the modulus of elasticity of a bone, comprising the steps of:
   (a) applying an ultrasound beam through a limb from a transmitting transducer to a receiving transducer;
   (b) measuring the flight times, $T_s$ for an ultrasound beam along a first path through the cortex of the bone, and $T_m$ along a second path through the cortex and medulla of said bone;
   (c) calculating the diameter X of the bone from the external diameter of the limb minus a predetermined constant representing the thickness of skin and flesh;
   (d) calculating the apparent velocity $C_a$ from X divided by $T_s$;
   (e) calculating the mean velocity V from X divided by $T_m$;
   (f) calculating the cortical bone velocity $C_{bE}$ from a predetermined function f multiplied by $C_a$;
   (g) determining the ratio R of the diameter of the medulla to the diameter of the cortex;
   (h) estimating the cross-sectional area $CSA_E$ of the bone from the values of the diameter X, the ratio R and from a predetermined amount;
   (i) determining the bone mineral content BMC;
   (j) determining the estimated compact bone density $CBD_E$ from said estimated cross-sectional area $CSA_E$ and from said determined bone mineral content BMC and
   (k) determining an estimate of the modulus of elasticity from the product of $CBD_E$ and the square of $C_{bE}$.

3. The method of claim 2, wherein said predetermined amount constant for determining the diameter X is determined from examination of skin and flesh thicknesses of a multiplicity of said limbs.

4. The method of claim 3 wherein said function f being empirically determined from $$\sqrt{1 - R_c^2} + R_c \cdot \arcsin R_c,$$

where $R_c$ is a corrected value of R using an empirical formula such as $R_c = 0.79 R (0.6 + 0.15R)$, said estimated cross-sectional area $CSA_E$ being determined from $M \cdot \pi/4 \cdot X^2(K - (L \cdot R^2))$, where K is an ovality factor for the external cortical bone cross section, L is an ovality factor for the medulla and M is a factor to take account of the area of the splint bones (MC2 and MC4), each of said factors being experimentally determined constants.

5. The method of claim 4, wherein said bone mineral content BMC is determined using a bone densitometer.

6. An apparatus for determining in vivo an estimate of the modulus of elasticity of a bone comprising transducer means for transmitting and receiving an ultrasound beam through the bone along a first path through the cortex of said bone and along a second path through the cortex and medulla of said bone, means for measuring the distance between said transducers and for subtracting from that distance an estimate of the thickness of an overlying tissue to obtain a measure of the diameter of said bone, means for determining the time of transmission of said ultrasound beam along said first and second paths, means for calculating the velocity of said beam along said first and second paths and for calculating an estimate of the transverse cortical bone velocity and the ratio of the diameter of the medulla to the diameter of the cortex, and means for calculating an estimate of the cross-sectional area of the cortex and for calculating from this information and from a separately derived measurement of the mineral content of said bone an estimate of the modulus of elasticity of the bone.

* * * * *